United States Patent
Wu et al.

(10) Patent No.: US 8,145,298 B2
(45) Date of Patent: Mar. 27, 2012

(54) ELECTRONIC INPUT DEVICE WITH PIEZOELECTRIC SENSOR

(75) Inventors: Tung-Ke Wu, Taipei (TW); Min-Chieh Hsieh, Taipei (TW)

(73) Assignee: ASUSTeK Computer Inc., Taipei (TW)

( * ) Notice: Subject to any disclaimer, the term of this patent is extended or adjusted under 35 U.S.C. 154(b) by 749 days.

(21) Appl. No.: 12/289,009

(22) Filed: Oct. 17, 2008

(65) Prior Publication Data

US 2009/0105553 A1    Apr. 23, 2009

(30) Foreign Application Priority Data

Oct. 18, 2007    (TW) ................................ 96139060 A

(51) Int. Cl.
*A61B 5/04* (2006.01)
*A61B 5/05* (2006.01)
*A61B 5/103* (2006.01)
*A61B 5/117* (2006.01)

(52) U.S. Cl. .................. 600/547; 600/546; 600/587
(58) Field of Classification Search .................. 600/546, 600/547, 554, 587
See application file for complete search history.

(56) References Cited

U.S. PATENT DOCUMENTS

| | | | | |
|---|---|---|---|---|
| 6,961,601 B2* | 11/2005 | Matthews et al. | ............. | 600/372 |
| 7,173,437 B2* | 2/2007 | Hervieux et al. | ............. | 324/663 |
| 7,245,956 B2* | 7/2007 | Matthews et al. | ............. | 600/382 |
| 7,288,075 B2* | 10/2007 | Parihar et al. | ................ | 600/590 |
| 7,435,232 B2* | 10/2008 | Liebschner | .................... | 600/587 |
| 7,463,917 B2* | 12/2008 | Martinez | ........................ | 600/395 |
| 7,904,180 B2* | 3/2011 | Juola et al. | .................... | 607/142 |
| 2003/0036691 A1* | 2/2003 | Stanaland et al. | ............ | 600/372 |
| 2005/0113691 A1* | 5/2005 | Liebschner | .................... | 600/437 |
| 2008/0293491 A1* | 11/2008 | Wu et al. | ......................... | 463/37 |
| 2009/0096748 A1* | 4/2009 | Wu | ................................ | 345/157 |
| 2009/0105553 A1* | 4/2009 | Wu et al. | ....................... | 600/300 |
| 2009/0115727 A1* | 5/2009 | Wu | ................................ | 345/163 |
| 2011/0050615 A1* | 3/2011 | Wu | ................................ | 345/173 |
| 2011/0080370 A1* | 4/2011 | Wu | ................................ | 345/174 |

FOREIGN PATENT DOCUMENTS

| | | |
|---|---|---|
| CN | 1220133 A | 6/1999 |
| CN | 1688961 A | 10/2005 |
| TW | I233829 | 6/2005 |
| TW | 200739399 | 10/2007 |

* cited by examiner

*Primary Examiner* — Jeffrey G Hoekstra
(74) *Attorney, Agent, or Firm* — Muncy, Geissler, Olds & Lowe, PLLC

(57) ABSTRACT

An electronic input device with piezoelectric sensor is provided, the electronic input device includes a housing, a piezoelectric sensing layer provided on the surface of the housing, an electrode plate provided and served to cover on top of the piezoelectric sensing layer. When a user's skin is in contact with the electrode plate, galvanic skin signals that represent the user's physiology status are transferred to the input device, meanwhile the piezoelectric sensing layer sends piezoelectric signals corresponding to the pressing level pressed by the user. When the piezoelectric sending layer is pressed to a proper level, effective galvanic skin signals are determined to the input device.

9 Claims, 4 Drawing Sheets

ELECTRONIC INPUT DEVICE WITH PIEZOELECTRIC SENSOR

RELATED APPLICATIONS

This application claims priority to Taiwan Application Serial Number 96139060, filed Oct. 18, 2007.

BACKGROUND

1. Field of Invention

The present invention relates to an input device, more particularly to an electronic input device with piezoelectric sensor.

2. Description of Related Art

A conventional art of galvanic skin response (GSR) is often adopted in a physiology measuring device used to measure the electrical resistance of the skin generated due to vasoconstriction, vasodilatation or secretion of the sweat gland when a person has emotional arousal. When the measuring device is in contact with human's skin, physiological pressure and emotion can therefore be quantified by analyzing the changes of the electrical resistance of the human's skin.

Skilled people in the art have adopted the above mentioned measuring device on surfaces of an electronic input device, e.g. a mouse, a keyword or a telephone. So when a user touches electrodes provided on the surfaces of the input devices, the current physiology status of the user is measured and proper relative information is also obtained. Thus a purpose of monitoring the user's physiology status is achieved (e.g. sending a signal indicating that the user needs a rest), or a purpose of indicating the user to operate the electronic input device is achieved (e.g. after sensing a command is finished then another command is proceed).

However, since not every user uses an input device with same operating habit, when they are using the input device, the pressing levels on the galvanic skin electrodes are varied. That is, when the areas of the electrodes on which a user's skin touches and the applied pressure are changed, the measured galvanic skin resistance is therefore changed. Hence, both the contact areas of the electrodes and the pressure applied on the electrodes need to be put into considerations for obtaining a more effective and accurate data, otherwise the operations of monitoring or indicating according to the invalid data are worthless.

SUMMARY

The present invention provides an electronic input device with piezoelectric sensor, for obtaining more effective and accurate piezoelectric data so the electronic input device can monitor physiology statuses or indicate operation procedures with respect to the precision data.

The electronic input device with piezoelectric sensor provided by the present invention comprises a piezoelectric sensing layer provided on a surface of a housing of the electronic input device. The piezoelectric sensing layer is electrically connected to a piezoelectric controlling/measuring circuit provided in the housing. The electrode plate is provided on top of the piezoelectric sensing layer, and electrically connected to a galvanic skin controlling circuit provided in the housing. When a user's skin is in contact with the electrode plate, galvanic skin signals measured by the electrode plate are transferred to the galvanic skin controlling circuit. Meanwhile corresponding piezoelectric signals are transferred to the piezoelectric measuring/controlling circuit by the piezoelectric sensing layer depending on the level of pressing the piezoelectric sensing layer via the electrode plate pressed by the user. When the piezoelectric sensing layer is pressed to a preset level, effective galvanic skin signals are determined to provide the input device.

According to one preferred embodiment of the present invention, plural piezoelectric sensing layers can be provided on the surface of the housing, each of the piezoelectric sensing layers is individually and electrically connected to the piezoelectric measuring/controlling circuit. When the piezoelectric sensing layers are pressed by a user, the pressed piezoelectric sensing layers respectively send different pressing level of piezoelectric signals to the piezoelectric measuring/controlling circuit, and the piezoelectric signals are received by a central processing circuit then are saved in a memory. Thus, information of the area, the shape and the center of applied pressure of the user-pressed portion of each of the piezoelectric sensing layers are recorded for future use.

For a conventional mechanical press-sensing fashion used for detection, when being operated, the current is varied due to the differences of the area of electrode touched by a user and the applied pressure, accordingly obtaining effective data is not likely to be achieved. The present invention utilizes the high sensitivity property of piezoelectric sensing material, so highly reliable galvanic skin data is obtained via an electronic input device. According to a preferred embodiment of the present invention, the electronic input device with piezoelectric sensor is not only simple in structure and assembly but also capable of effectively obtaining precise galvanic skin signals.

BRIEF DESCRIPTION OF THE DRAWINGS

The structure and the technical means adopted by the present invention to achieve the above and other objectives can be best understood by referring to the following detailed description of the preferred embodiments and the accompanying drawings, where.

DESCRIPTION OF THE PREFERRED EMBODIMENTS

Figure 1:
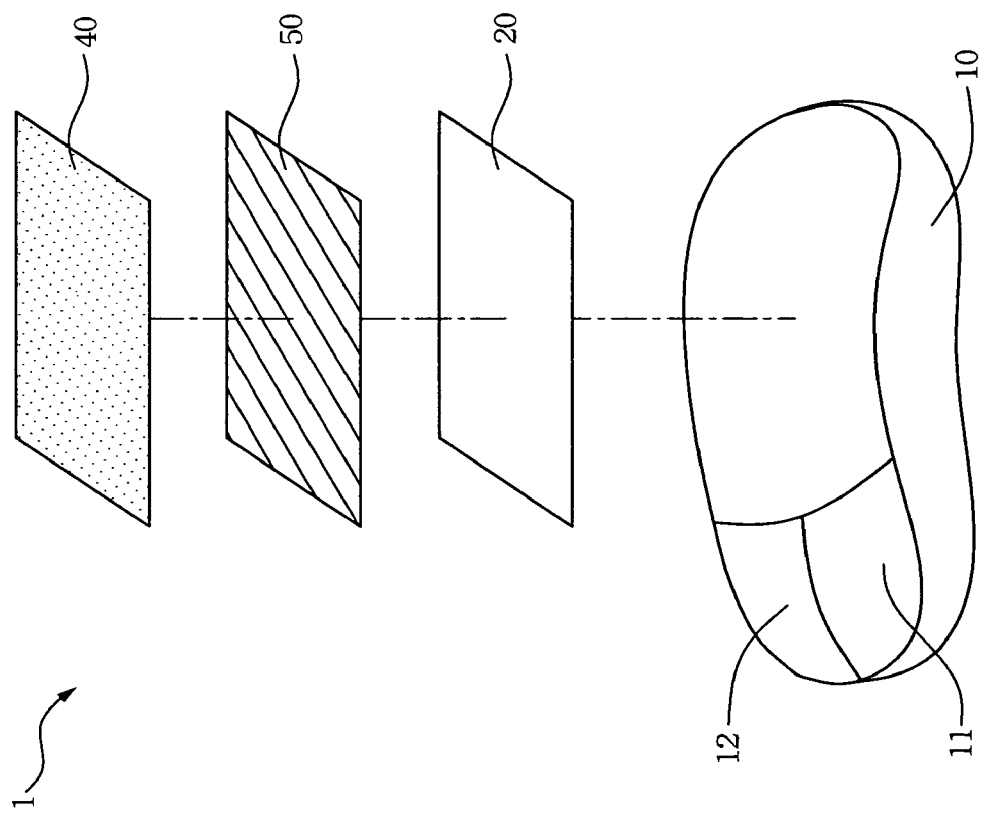
FIG. 1 is a partial exploded view of an electronic input device as a mouse device of a preferred embodiment of the present invention.

It is to be understood that the following disclosure provides one or more preferred embodiments or examples for implementing different features of the disclosure. Specific examples of components and arrangements are described below to simplify the present disclosure. Of course, these are merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Figure 2:
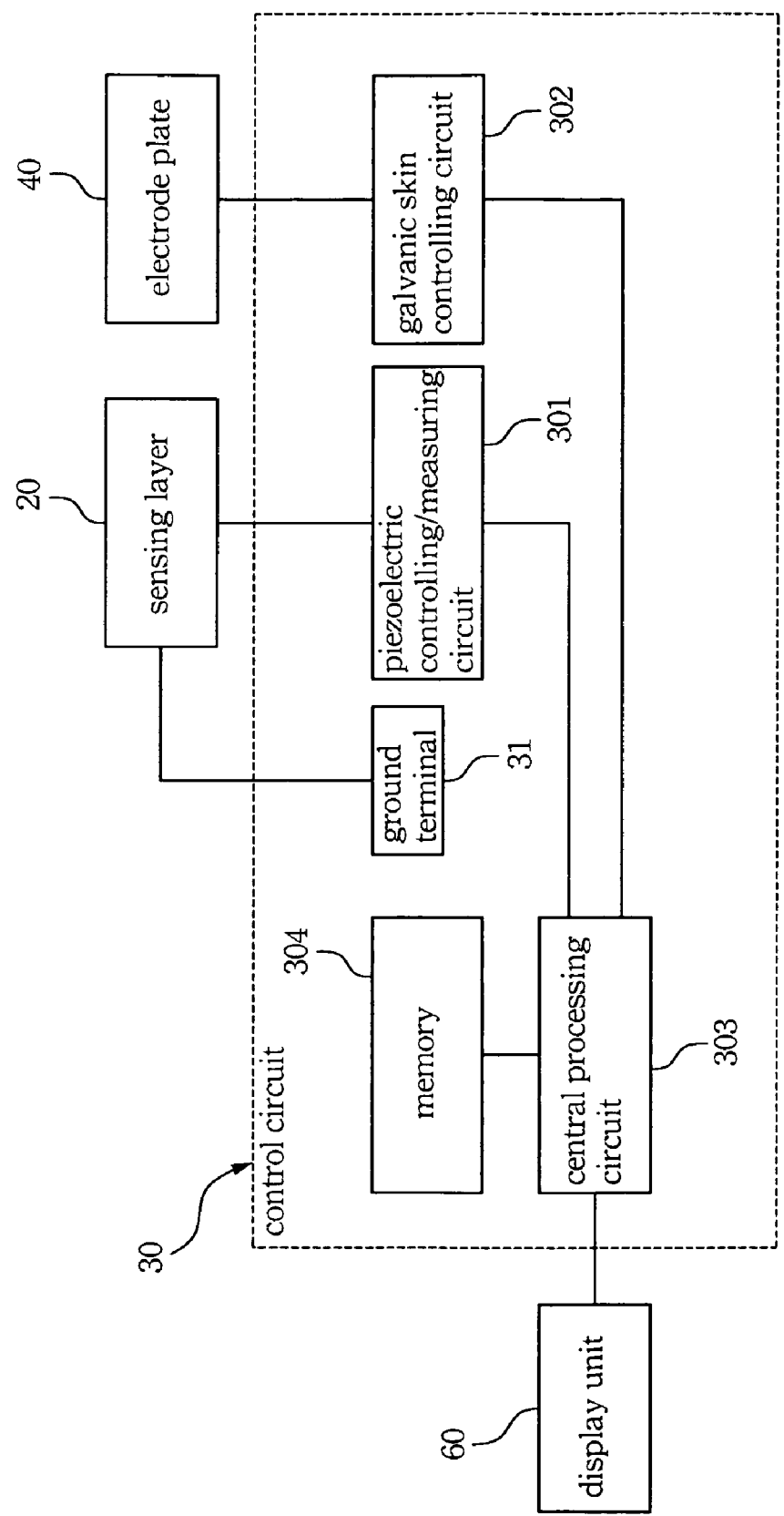
FIG. 2 is an electrical block diagram of the electronic input device provided by the present invention.

Referring to FIG. 1 and FIG. 2, wherein FIG. 1 is a partial exploded view of a mouse device, FIG. 2 is an electrical block diagram of the input device provided by the present invention. As shown in FIG. 1, a surface of a housing 10 of a mouse device 1 is provided in sequence with a piezoelectric sensing layer 20, an insulation layer 50 and an electrode plate 40, and a control circuit 30 (not shown in FIG. 1) is further provided inside the housing 10.

Referring to FIG. 4 to FIG. 8, the electronic input device provided by the present invention can be implemented on a mouse device 1, a keyboard device 2 (FIG. 4), a joystick device 3 (FIG. 5), a track ball device 4 (FIG. 6), a handwriting device 5 (FIG. 7) or an interne telephone device 6 (FIG. 8) etc.

In this embodiment, the piezoelectric sensing layer 20 includes a piezoelectric sensing material which is preferable to be quartz, $LiNbO_3$, $LiTaO_3$, AlN, ZnO, $BaTiO_3$, $PbZrTiO_3$ or a polymer such as polyvinylidene difluoride (PVDF).

Wherein the piezoelectric sensing layer 20 in FIG. 2 is electrically connected to a piezoelectric controlling/measuring circuit 301 provided on the control circuit 30 inside the housing 10. The other surface of the piezoelectric sensing layer 20 is connected to a ground terminal 31, so that the piezoelectric sensing layer 20 and the piezoelectric controlling/measuring circuit 301 can be defined as one piezoelectric sensor (in this embodiment the piezoelectric controlling/measuring circuit 301 further includes a measure circuit). When the surface of the piezoelectric sensing layer 20 is pressed by an external pressure, a phenomenon of inter-exchange between mechanical energy and electrical energy is generated so as to obtain continually piezoelectric signals, and the piezoelectric signals are transferred to the piezoelectric controlling/measuring circuit 301. The relationship between the generated piezoelectric signals and the pressure applied are an invertible function, or a linear function under other conditions. Therefore a measured voltage value can be served to calculate the original pressure applied on the piezoelectric sensing layer 20.

The electrode plate 40 is electrically connected to a galvanic skin controlling circuit 302 of the control circuit 30 provided inside the housing 10, so when a user's skin is in contact with the electrode plate 40, galvanic skin response values (GSR values) received by the electrode plate 40 are transferred to the galvanic skin controlling circuit 302 via the user's skin. The electrode plate 40 is preferably made of a conductive material such as stainless steel or chloride silver. The quantity of the electrode plate 40 provided can be more than one, in other words the plural electrode plates 40 can be provided on the surface of the housing 10. In this embodiment, the area of the piezoelectric sensing layer 20 is substantially the same as the area of the electrode plate 40, and at least one insulation layer 50 is provided as an electrical insulation between the electrode plate 40 and the piezoelectric sensing layer 20. Therefore, the piezoelectric sensing layer 20 would not be interfered by the electrode plate 40.

In the embodiment, beside the provided electrode plate 40 served as a piezoelectric measuring electrode, a ground electrode plate (not shown) can be further provided. Regardless of the insulation layer 50, the ground electrode plate can be directly in contact with the piezoelectric sensing layer 20.

Refer to FIG. 1 and FIG. 2, a central processing circuit 303 is further provided on the control circuit 30 inside the housing 10. The central processing circuit 303 is respectively and electrically connected to the piezoelectric controlling/measuring circuit 301 and the galvanic skin controlling circuit 302, and a valid range of piezoelectric signal, e.g. 50 mV, is preset in the central processing circuit 303. Thus, when the central processing circuit 303 simultaneously receives at least one piezoelectric signal and galvanic skin signal, the central processing circuit 303 determines if the received piezoelectric signal is within the valid range of piezoelectric signal; if so, the galvanic skin signals are calibrated then outputted, if not, the galvanic skin signals are ignored.

The central processing circuit 303 can be served to quantify the piezoelectric signal to patterns or numbers shown on a display unit 60, e.g. an external display device or a screen provided on the housing 10, for providing references to users. When the electrode plate 40 is in contact with and is pressed by a user via his/her skin, the piezoelectric sensing layer 20 provided below the electrode plate 40 is also pressed via the electrode plate 40 so as to generate a piezoelectric signal. When the central processing circuit 303 determines that the generated piezoelectric signal is not within the preset valid range of piezoelectric signal, a warning signal is therefore generated via the display unit 60, so a user is informed whether the applied pressure is too small or too high.

On the other hand, when the central processing circuit 303 determines that the generated piezoelectric signal is within the preset valid range of piezoelectric signal, the galvanic skin signals corresponding to the piezoelectric signal are saved in a memory 304 by the central processing circuit 303 so subsequent analyze can be operated. Therefore when the piezoelectric sensing layer 20 is properly pressed, the input device 1 is provided with effective galvanic skin signals, so physiology of the user is monitored (for example sending a signal indicating that the user needs a rest), or indicating an operating procedure (for example after sensing a command is finished then another command is proceed).

Figure 3:
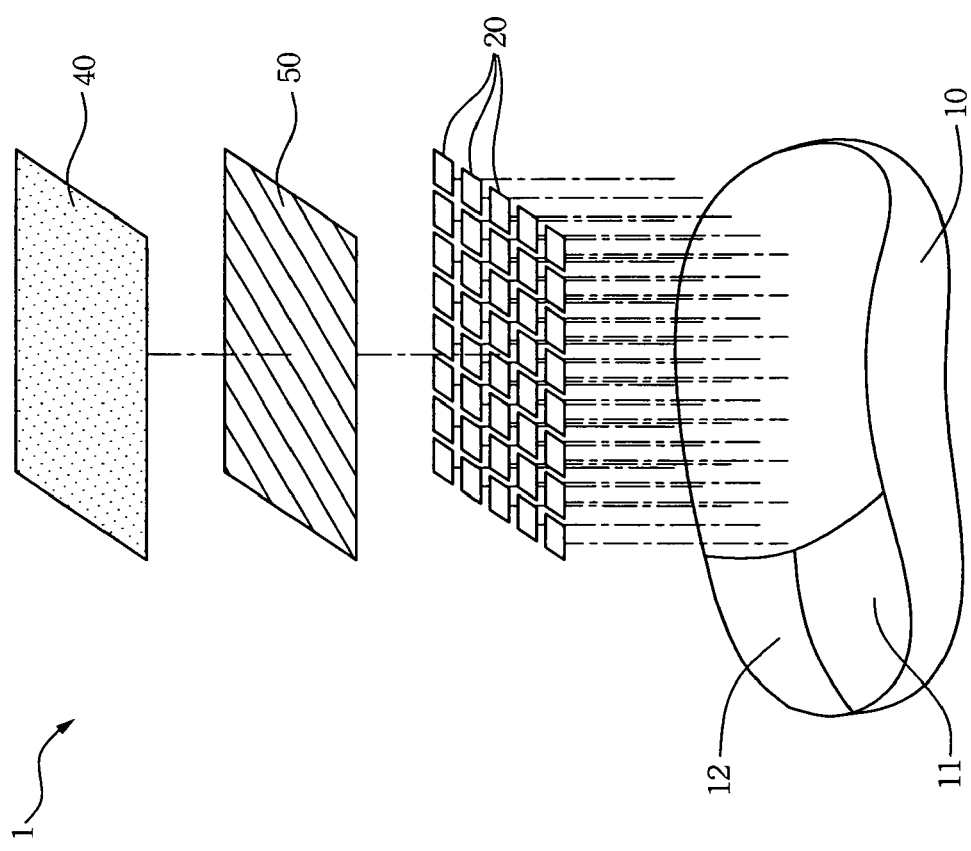
FIG. 3 is a partial exploded view of an electronic input device as a mouse device of another preferred embodiment of the present invention.
Figure 4:
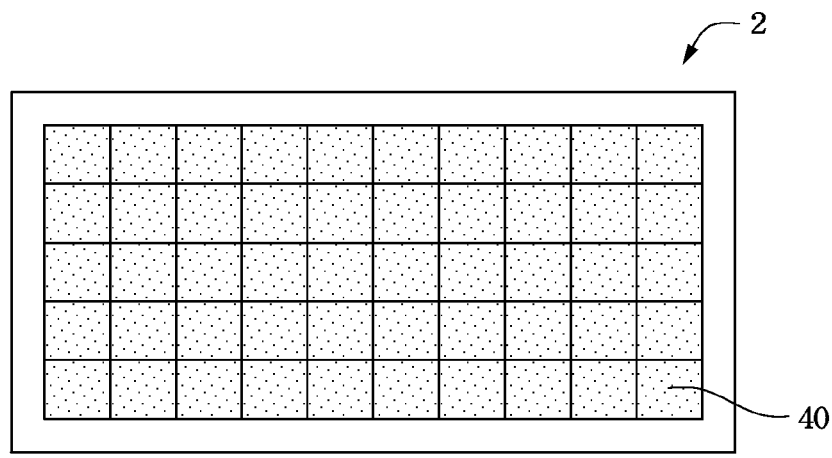
FIG. 4 is a front view of an electronic input device as a keyboard of the other embodiment of the present invention.
Figure 5:
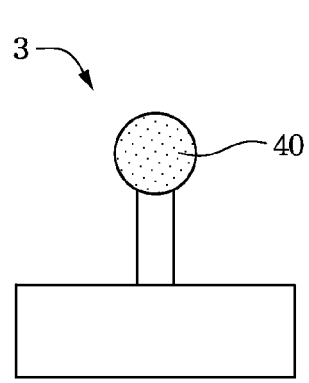
FIG. 5 is a side view of an electronic input device as a joystick device of the other embodiment of the present invention.
Figure 6:
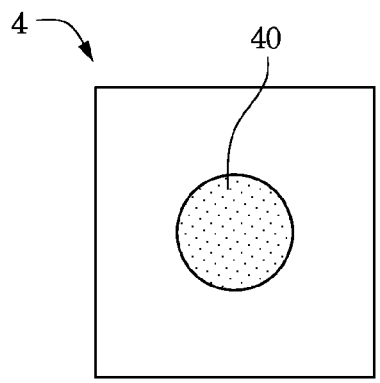
FIG. 6 is a front view of an electronic input device as a track ball device of the other embodiment of the present invention.
Figure 7:
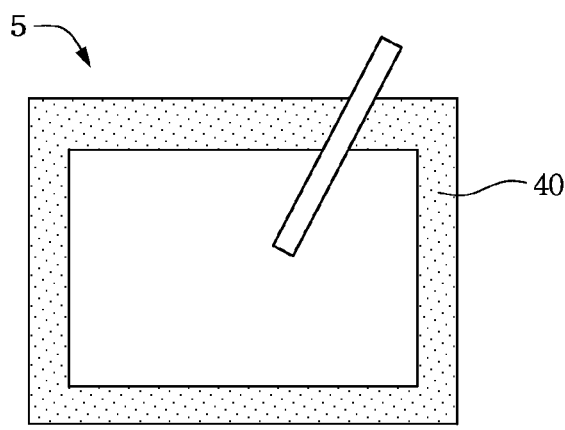
FIG. 7 is a front view of an electronic input device as a hand writing device of the other embodiment of the present invention.
Figure 8:
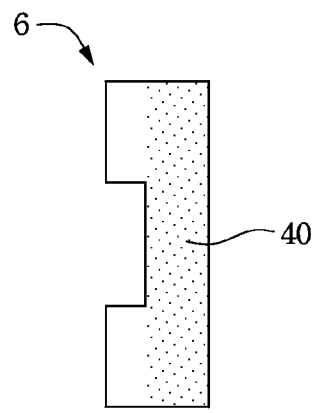
FIG. 8 is a side view of an electronic input device as an internet telephone device of the other embodiment of the present invention.

In another embodiment of the present invention, referring to FIG. 2 and FIG. 3, wherein FIG. 3 is a partial exploded view of a mouse device; the quantity of piezoelectric sensing layer 20 can be more than one therefore plural piezoelectric sensing layers 20 are provided on the surface of the housing 10 in a matrix arrangement. Each of the piezoelectric sensing layers 20 is individually and electrically connected to the piezoelectric controlling/measuring circuit 301. When the piezoelectric sensing layers 20 are pressed by a user, the pressed piezoelectric sensing layers 20 individually send a piezoelectric signal to the piezoelectric controlling/measuring circuit 301, and the piezoelectric signals are received by the central processing circuit 303. Then the piezoelectric signals are saved in the memory 304, so information of which body portion of the user (finger(s), palm(s)) is used to press each of the piezoelectric sensing layers 20 and information of the area. The shape and the center of applied pressure of the user-pressed portion of each of the piezoelectric sensing layers 20 are recorded for future use. Regardless of that if each of the piezoelectric signals generated by the pressed piezoelectric sensing layers 20 is within the preset valid range of piezoelectric signal, the piezoelectric signals are all saved in the memory 304.

After obtaining the information of the area, the shape and the center of applied pressure of the user-pressed portion of each of the piezoelectric sensing layers, the appearance of the housing 10 of the input device 1 can be designed to be more ergonomic for matching the using habits of the users so more accurate physiology information can be obtained.

The described application of the piezoelectric sensor is illustrated via the palm of the user being in contact with the surface of the housing of the mouse device, but surfaces of a left key 11 and a right key 12 of the mouse device also can be respectively provided with a piezoelectric sensing layer 20, an insulation layer 50 and an electrode plate 40 in turn, to serve as another approach to obtain the user's physiology information.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An electronic input device with piezoelectric sensor, comprising:
    a housing;
    a piezoelectric sensor comprising:
    a piezoelectric sensing layer provided on an outer surface of the housing; and
    a piezoelectric controlling/measuring circuit provided inside the housing and electrically connected to the piezoelectric sensing layer;
    a galvanic skin controlling circuit provided inside the housing;
    an electrode plate disposed on the piezoelectric sensing layer and electrically connected to the galvanic skin controlling circuit, wherein the piezoelectric sensing layer is disposed between the electrode plate and the housing; and
    a central processing circuit provided inside the housing and electrically connected to the piezoelectric controlling/measuring circuit and the galvanic skin controlling circuit,
    wherein when a skin portion is contacted with the electrode plate and the piezoelectric sensing layer, a galvanic skin signal of the skin portion is transferred to the galvanic skin controlling circuit by the electrode plate, a piezoelectric signal is transferred to the piezoelectric controlling/measuring circuit by the piezoelectric sensing layer, and the central processing circuit determines whether outputting the galvanic skin signal or not according to the piezoelectric signal.

2. The electronic input device as claimed in claim 1, wherein a valid range of the piezoelectric signal is preset in the central processing circuit; after receiving the piezoelectric signal, the central processing circuit determines whether the piezoelectric signal is within the valid range of piezoelectric signal; if so, the galvanic skin signal is calibrated then outputted, if not, the galvanic skin signal is ignored.

3. The electronic input device as claimed in claim 1, wherein a plurality of the piezoelectric sensing layers are provided on the outer surface of the housing in a matrix arrangement.

4. The electronic input device as claimed in claim 3, wherein each of the piezoelectric sensing layers is individually and electrically connected to the piezoelectric controlling/measuring circuit; when the piezoelectric sensing layers are pressed, corresponding piezoelectric signals are respectively generated.

5. The electronic input device as claimed in claim 1, wherein the piezoelectric sensing layer includes a piezoelectric sensing material selected from the group consisting of quartz, LiNbO3, LiTaO3, AlN, ZnO, BaTiO3, and PbZrTiO3.

6. The electronic input device as claimed in claim 5, wherein the piezoelectric sensing material is a polymer.

7. The electronic input device as claimed in claim 6, wherein the polymer is polyvinylidene difluoride (PVDF).

8. The electronic input device as claimed in claim 1, wherein at least one insulation layer is further provided between the electrode plate and the piezoelectric sensing layer.

9. The electronic input device as claimed in claim 1, wherein the electronic input device is a mouse device, a keyboard device, a joystick device, a track ball device, a hand writing device or an interne telephone device.

* * * * *